United States Patent [19]

Schneider

[11] 4,066,505

[45] Jan. 3, 1978

[54] PROCESS FOR EXTRACTING A POLYPEPTIDE FROM AN AQUEOUS SOLUTION

[75] Inventor: Michel Schneider, Grand-Lancy, Switzerland

[73] Assignee: Battelle Memorial Institute, Switzerland

[21] Appl. No.: 667,258

[22] Filed: Mar. 16, 1976

[30] Foreign Application Priority Data

Mar. 18, 1975 Switzerland .......................... 3468/75

[51] Int. Cl.$^2$ ........................... C07G 7/02; C07G 7/00
[52] U.S. Cl. .................................... 195/66 R; 195/63; 260/112 R
[58] Field of Search ................. 195/66 R, 66 A, 66 B, 195/63, 68; 260/112 R

[56] References Cited

U.S. PATENT DOCUMENTS

| 3,834,990 | 9/1974 | Werle et al. ................. 260/112 R X |
| 3,983,001 | 9/1976 | Coupek et al. .................... 195/66 R |

*Primary Examiner*—Lionel M. Shapiro
*Attorney, Agent, or Firm*—Robert E. Burns; Emmanuel J. Lobato; Bruce L. Adams

[57] ABSTRACT

A polypeptide is extracted from an aqueous solution by a process in which a water-soluble macromolecular complex (I) of macromolecules covalently boned to molecules of at least one compound capable of fixing the polypeptide in a selective, reversible and non-destructive manner, is selectively reacted with the polypeptide in the solution to fix the polypeptide by forming in solution a complex (II); and the complex (II) is separated from the solution and dissociated into polypeptide molecules and complex (I) molecules, and the polypeptide is isolated.

8 Claims, No Drawings

PROCESS FOR EXTRACTING A POLYPEPTIDE FROM AN AQUEOUS SOLUTION

This invention relates to a process for extracting a polypeptide from an aqueous solution, in particular for extracting an enzyme.

Over the last few years the use of enzymes to carry out industrial chemical processes has become more widespread. This can mainly be attributed to the development of processes for fixing enzymes on a support or in a solid matrix, consisting for example of a synthetic resin, which enables the enzyme to be recovered easily after use and, in many cases, also enables the life of the enzyme to be prolonged.

Industrial processes in which enzymes are used include, for example, separation of the L-isomer from DL-methionine using an acylase fixed on a polyacrylamide; the production of fructose from glucose using glucose isomerase; the removal of lactose from milk or whey by means of lactase fixed on a support; and the production of penicillin derivatives using penicillin amidase.

In these types of processes, the fixing of the enzyme on a support enables the specific consumption of the enzyme to be considerably reduced, but the cost price of the product is generally of the same order as when it is manufactured by a non-enzymatic process. However, it has been calculated that a decrease of the order of 30% in the cost price of the enzyme would make enzymatic processes competitive with other known processes.

Except for some rare exceptions such as the proteases, amylases and glucoamylases, enzymes are expensive. The cost price of enzymes may be reduced in various ways, in particular by a suitable choice of enzyme sources and by producing new mutant strains thereof. However, irrespective of the origin of the enzyme, at the present time one is confronted by the difficulty of extracting the enzyme from a solution (crude extract) which generally contains only 10,000 to 100,000 enzyme units per liter, in other words at most a few grams per liter (an enzyme unit is generally defined as the amount of enzyme needed to convert a micromole of substrate per minute under optimum reaction conditions).

Two types of processes for extracting enzymes from their solutions (crude extracts) are known.

The processes belonging to the first type (so-called "classical" processes) consist of firstly removing the nucleic acids present in the crude extract by adding suitable substances such as protamine sulphate or nuclease, next fractionally precipitating the proteins by means of mineral salts such as ammonium sulphate or certain organic compounds such as ethanol, acetone or polyhydroxy alcohols, and then separating the enzymes from the other proteins by carrying out a series of chromatographs.

The processes of the second type (affinity chromatography) consist of selectively extracting the enzyme by contacting the crude extract directly with a solid substance such as cellulose or a synthetic resin to which are covalently bonded molecules of a specific inhibitor for this enzyme, and then eluting the enzyme.

A process belonging to this second type is described for example in the German Offenlegungschrifts Nos. 1,517,753 and 1,768,934. According to this process, the solid substances to which the enzyme inhibitor molecules are bonded is used either in a chromatography column or in suspension in the solution containing the enzyme which it is desired to extract.

The processes of the first type have the disadvantage that they require, for a relatively small weight of enzyme, large amounts of ammonium sulphate and also the treatment of large volumes of aqueous solution, while achieving only a slight purification of the enzyme. The costs involved in operating these processes are thus high.

The processes of the second type also have disadvantages. Where the solid substance to which the molecules of inhibitor are bonded is used in a chromatography column, high molecular weight substances such as proteins which are present in the solution rapidly saturate or block up the column. Where the solid substance is used in suspension in the solution, only a small part of the inhibitor molecules can be used to fix enzyme molecules since the solution is only in contact with the external surface of the particles of the solid substance, and possibly with a small proportion of the surface of any pores these particles may have. The yield from these processes, expressed as the ratio of the amount of enzyme extracted to the amount of inhibitor required, is thus relatively low, which is also a factor which raises their operating costs.

An object of the invention is to obviate the disadvantages which have just been mentioned by largely reducing the cost of extracting polypeptides from aqueous solutions, and in the particular the cost of extracting enzymes from "crude extracts."

To this end, the process according to the invention is a process for extracting the polypeptide from an aqueous solution, in which a water-soluble macromolecular complex (I) of macromolecules covalently bonded to molecules of at least one compound capable of fixing the polypeptide in a selective, reversible and non-destructive manner, is selectively reacted with the polypeptide in the solution to fix the polypeptide by forming, in solution, a complex (II); and the complex (II) is separated from the solution and dissociated into polypeptide molecules and complex (I) molecules, and the polypeptide is isolated.

In order to extract an enzyme from an aqueous solution such as a "crude extract," as the compound capable of fixing the polypeptide there may be used a compound selected from reversible inhibitors and substrates and substrate analoguse for this enzyme.

The expression "crude extract" is understood to mean an aqueous solution containing, in addition to the enzyme or enzymes it is desired to extract, other proteins, nucleic acids, metabolites, mineral salts, polysaccharides and many other inorganic and organic substances. "Crude extracts" from any source may be used, in particular those which are obtained, in a manner known per se, from microorganism culture after breaking down the cells and extracting proteins, or from animal tissue homogenates, or from plant extracts.

The term "complex" used herein in intended to mean a combination of molecules bonded together and is not intended to convey any particular mode of bonding. Thus the complex (I) is a covalently bonded macromolecule while complex (II) may be a less clearly defined combination of complex (I) with the polypeptide in solution.

The expression "reversible enzyme inhibitor" is intended to mean a compound whose molecules have the property that they can fix themselves selectively, reversibly and non-destructively to a given enzyme or to enzymes belonging to a well-defined class, by means of a chemical bond localised at a well-defined point in the molecule of the enzyme, thereby "destroying" or reducing the catalytic activity of the enzyme. Since this fixation is reversible and non-destructive it neither destroys nor damages the enzyme, and the molecules of the latter may finally be separated from the inhibitor molecules while recovering their original catalytic activity.

The expression "substrate" is intended to mean the compound in respect of which the enzyme exhibits its specific catalytic activity. Such a compound may be used in the case where it can attach itself to the enzyme under conditions which are adapted to temporarily inhibit or suppress the catalytic activity of the enzyme, for example in the absence of a given metal ion, below a certain temperature, in a well-defined pH range, etc. A "substrate" may also be used in the case where the enzyme reacts only in the simultaneous presence of two substrates (one of which is an electron donor for example, the other being an electron acceptor) and where one of these two substrates is nevertheless capable of fixing itself sufficiently to the enzyme in the absence of the other substrate.

The expression "pseudo-substrate" or "substrate analogue" is intended to mean a compound which is sufficiently similar in its chemical structure to the specific substrate of the enzyme for it to become fixed to the enzyme, but without the latter having any significant catalytic activity towards it.

Of course, as well as the "substrates" and the "substrate analogues," the "reversible enzyme inhibitors" may have an aptitude for selective, reversible and non-destructive fixation, not only as regards a given enzyme but also as regards enzymes belonging to one or several families.

As a reversible enzyme inhibitor, there may for example be used one of the following compounds: p-aminophenyl-thiogalactoside (a β-galactosidase inhibitor), and p-aminobenzoic acid (a tyrosinase inhibitor).

As a substrate, there may for example be used poly-L-lysine (a substrate for pepsin), nicotinamide adenine dinucleotide or "NAD" (an electron acceptor substrate for enzymes belonging to the dehydrogenase family, whose enzymatic activity is exerted only in the presence of "NAD").

As a substrate analogue, there may for example be used D-asparagine (a substrate analogue for L-asparagine).

Examples of the use of inhibitors, substrates and substrate analogues for enzymes, for use in the purification of enzymes by the affinity chromatography process and by using these compounds in the grafted state on solid synthetic resins, are given in particular in the following book: "Biological aspects of reactions on solid supports" by George R. Stark (1971 — Academic Press, New York and London), Chapter 2 by Pedro Cuatrecasas, and in the following publication: M. Wilchek and W. B. Jakoby, Methods in Enzymology, Vol. 34, p. 3 (1974).

In order to form the complex (I), molecules of the said compound capable of fixing the polypeptide may be grafted onto a suitable polymer substance. The complex (I) may also be formed by polymerising a monomer whose molecules consist of a polymerisable unit, for example a vinyl group, to which is attached by covalent bonds at least one molecule of the compound capable of fixing the polypeptide.

A water-soluble substance, for example carboxymethyl cellulose, polyacrylamide, polyethylene glycol, a polyamine, polyvinyl alcohol, dextran, etc., may be used as the polymer substance onto which is grafted the compound capable of fixing the enzyme.

The molecules of the compound capable of fixing the enzyme may be grafted onto the molecules of the polymer substance either directly or via molecules of an auxiliary compound, the latter being linear and having a suitable chain length (for example molecules which at least in part consist of an aliphatic hydrocarbon chain). The molecules of this auxiliary compound act as spacing arms or anchoring arms in the complex (I) and enable enzyme molecules to become attached to the molecules of complex (I); in the absence of such spacing arms certain enzyme molecules would not be able to become attached to the complex (I) on account of steric hindrance.

The book mentioned above describes numerous examples of the way in which molecules of at least one compound capable of fixing an enzyme can be grafted onto a synthetic polymeric organic material insoluble in water, as well as the case of direct grafting, and grafting via spacing arms or anchoring arms.

In order to carry out the process according to the present invention the same techniques as those described in the said book may be used, but instead using a polymer substance dissolved in water, in place of a solid material which is insoluble in water.

For example, molecules of p-aminophenyl-β-D-thiogalactopyranoside may be grafted on polyacrylamide, or molecules of p-aminophenol may be grafted on carboxymethyl cellulose via molecules of N-bromoacetyl ethylene diamine, or, again, molecules of p-aminobenzoic acid (tyrosinase inhibitor) may be grafted on polyacrylamide via molecules of 6-aminocaproic acid.

To react the complex (I) with the polypeptide being extracted, any suitable procedure may be adopted, for example by simply mixing an aqueous solution of the complex (I) with the aqueous solution of polypeptide or, again, by varying at least one parameter such as the ionic strength, the temperature or the pH of the liquid medium containing the complex (I) and the polypeptide.

To separate the dissolved complex (II), any suitable procedure may be adopted, the procedure being selected depending on the nature and solubility of this complex as well as the composition and properties of the liquid medium containing the complex (II) and the polypeptide. The physico-chemical phenomenon involved in the precipitation of the complex may be a precipitation as such or a flocculation, depending on the case. This phenomenon may be example be produced by adding a suitable salt to the liquid medium, or, again, by modifying at least one parameter of the medium such as its temperature, pH or concentration.

In order to dissociate the separated complex (II) into molecules of polypeptide and molecules of complex (I) and then to separate the molecules of polypeptide from those of the complex (I), any suitable procedure which is known per se may be used, in particular re-dissolving the complex (II) after its precipitation and, if necessary, purification, and altering the ionic strength of the solution thus obtained, or, again, subjecting the latter to dialysis or ultra-centrifugation.

The following Examples illustrate the invention.

EXAMPLE 1

A. Preparation of the complex (I):
 a. Starting Substances Used
  A1: polyacrylamide (a water-soluble polymer formed from linear macromolecules having the repeating unit:

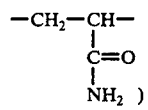

A2: methyl ester of polyacrylic acid (a polymer insoluble in water and formed from linear macromolecules having the repeating unit:

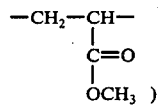

A3: acryloyl chloride (the monomeric compound of the formula:

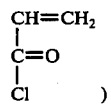

b. Operating Methods
  A1 and A2: reacting the macromolecular starting substance with hydrazine at a temperature of 50° C (A1) and 90° C (A2) respectively so as to obtain polyacrylamide hydrazide (a polymer formed from linear macromolecules having the repeating unit:

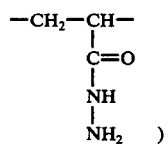

and then converting the polyacrylamide hydrazide into the corresponding azide derivative by reaction at 0° C in the presence of a mixture of hydrochloric acid and sodium nitrate, according to the reaction:

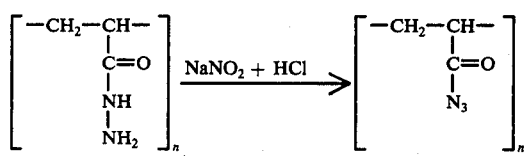

where $n$ represents the number of repeating units per molecule of the macromolecular substance, and, finally, reacting the polyacrylamide azide at 0° C with p-aminobenzoic acid in an aqueous medium having a pH of 9.4:

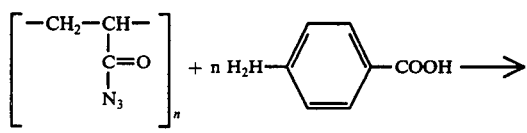

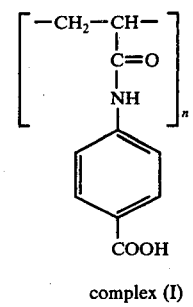

complex (I)

A3: reaction between acryloyl chloride and p-aminobenzoic acid:

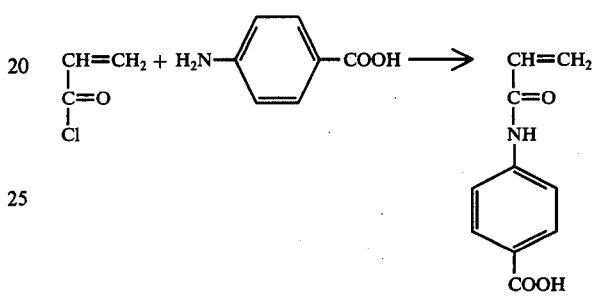

followed by polymerization of the monomer thus obtained, in aqueous medium under a nitrogen atmosphere and in the presence of ammonium persulphate, which catalyzes the polymerization.

The polymer obtained by the procedure of any one of the methods mentioned above is subjected to ultra-filtration on an ultra-filtration membrane which allows molecules having a molecular weight below 50,000 to pass through, (for example a membrane of the type commercially termed XM 50 and marketed by AMICON company) and the dissolved polymer fraction which passes into the filtrate is used.

B. Extraction of tyrosinase from an aqueous solution 30 mg of the macromolecular complex (I) obtained as described in A was dissolved in 100 ml of an aqueous saline solution (0.05 M NaCl) having a pH of 7.2 and containing 100 mg of bovine serum albumin and 1 mg of tyrosinase (enzymatic activity 900 units). After the complex (I) had completely dissolved the temperature of the liquid medium was lowered to 0° C and its pH was then slowly reduced to 4.5 by the gradual addition of an aqueous solution of citric acid. At the point when the pH value 4.5 was reached, the formation of a precipitate was observed (complex II). This precipitate was separated from the liquid phase by centrifugation at 2,000 rev/min and the centrifugation pellet was washed twice with a 0.5 M solution of sodium chloride while maintaining the pH at 4.5 and its temperature at 0° C. No enzymatic activity attributable to tyrosinase could be detected either in the supernatant liquid phase above the centrifugation pellet or in the wash waters from the pellet, while on the other hand the presence of bovine serum albumin could easily be detected in these liquids.

After the centrifugation pellet had been washed it was re-dissolved in 20 ml of an aqueous solution of sodium pyrophosphate containing 50 millimoles of the latter salt per liter and having a pH of 8.8, and the solution thus obtained was subjected to ultra-filtration through an ultra-filtration membrane which allows only molecules having a molecular weight below 50,000 to pass through.

Tyrosine remained in the retained fraction although the residue of the molecules of the complex (II), namely molecules of complex (I), passed into the filtrate, thus enabling them to be used again in another extraction operation.

The tyrosinase thus obtained had an enzymatic activity which corresponded to about 40% of that of the starting solution, while at the same time being mixed with 1.6 mg of proteins (amount measured by Lowry's method). The purification factor obtained was thus 25.

EXAMPLE 2

A. Preparation of the complex (I):
 a. Starting Substance
 carboxymethyl cellulose hydrazide (a water-soluble polymer):
 b. Operating Method
 Conversion of the carboxymethyl cellulose hydrazide into the corresponding azide derivative by reaction at 0° C in the presence of a mixture of hydrochloric acid and sodium nitrite and, finally, reacting the azide in an aqueous medium at pH 8.7 and always at 0° C, with a mixture of o-aminobenzoic acid and trypsin inhibitor, namely a soya extract (peptide type inhibitor having a molecular weight of the order of 23,000). (0.1 g of o-aminobenzoic acid and 0.1 g of soya inhibitor are used per 1 g of initial hydrazide derivative).

A water-soluble polymer is thus obtained which contains both molecules of o-aminobenzoic acid and molecules of trypsin inhibitor, i.e., soya extract, bonded to the polyanhydroglucose chain of the starting macromolecular substance by space arms of the formula —O—CH$_2$—CO—NH—.

B. Extraction of trypsin from an aqueous solution 20 mg of the macromolecular complex (I) obtained in the manner described in A were dissolved in 100 ml of an aqueous saline solution (0 04 M NaCl) having a pH of 7.2 and containing 100 mg of bovine serum albumin and 1 mg of trypsin (enzymatic activity: 7,200 units). After the complex (I) had completely dissolved, the temperature of the liquid medium was lowered to 0° C and its pH was then slowly reduced to 3.7 by adding an aqueous solution of acetic acid. A precipitate (complex II) was thus obtained which was separated from the liquid by centrifugation (2,000 rev/min), and the centrifugation pellet was washed with a solution of sodium chloride (0.5 M) while maintaining its pH at 3.7 and its temperature at 0° C. The centrifugation pellet thus washed was suspended in a 0.5 M solution of sodium chloride, and the pH of the suspension thus obtained was lowered to 2.2 by adding an aqueous solution of hydrochloric acid. The suspension was then centrifuged (2,000 rev/min) and the supernatant liquid phase was recovered. The enzymatic activity of the latter corresponded to about 23% of that of the starting solution, the supernatant containing 5.2 mg of proteins. The purification factor of the trypsin was thus 4.4.

EXAMPLE 3

A. Preparation of the complex (I)
 1 g of polyacrylamide azide obtained as described in Example 1 is reacted with an aqueous solution containing 0.1 g of o-aminobenzoic acid and 0.1 g of trypsin, in an aqueous medium having a pH of 8.2, and at 0° C.

B. Extraction of soya inhibitor from an aqueous solution

Using the complex (I) prepared as mentioned in A, a procedure similar to that described in Example 2 was adopted, but with 1 mg of trypsin-inhibiting soya extract, in place of trypsin in the aqueous starting solution. An aqueous solution was finally obtained having an inhibiting activity for the trypsin corresponding to about 28% of that for the starting solution, and containing 4.5 mg of proteins.

EXAMPLE 4

A. Preparation of the complex (I)
 N(ω-aminohexyl)-L-aspartic acid (a compound having the following formula:

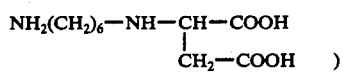

This monomer is then polymerized in an aqueous medium under a nitrogen atmosphere and in the presence of ammonium persulphate, which acts as a catalyst. The dissolved polymer thus obtained (complex I) is subjected to ultra-filtration through an ultra-filtration membrane whose pores have a size of 0.05 micron, and the retained fraction is preserved.

B. Extraction of asparaginase from an aqueous solution 30 mg of the macromolecular complex (I) obtained in the manner described in A were dissolved in 100 ml of an aqueous saline solution (0 05 M NaCl) having a pH of 7.2 and containing 100 mg of bovine serum albumin and 1 mg of asparaginase (enzymatic activity: 210 units).

The macromolecular complex (II) obtained by fixing asparaginase molecules to the complex (I) in solution was then precipitated by adjusting the pH of the liquid medium to 4.5, and the suspension thus obtained was centrifuged (2,000 rev/min). The centrifugation pellet was washed while maintaining its pH at 4.5, and was then dissolved in an aqueous saline solution O (0.04 mM NaCl; 0.01 mM sodium acetate) having a pH of 7.0. The solution thus obtained was subjected to ultra-filtration through a membrane having pores 0.05 micron in diameter, the retained fraction being washed with a sufficient amount of the aforementioned aqueous saline solution so that no more than traces of proteins appeared in the final filtrate. An aqueous solution having a pH of 7.0 and containing 70 millimoles of L-aspartic acid and 10 millimoles of sodium acetate per liter was then added to the retained fraction. Asparaginase was thus displaced from the complex (II) and this enzyme then appeared in the filtrate. An aqueous solution of asparaginase was thus obtained, having an enzymatic activity corresponding to 65% of that of the starting solution and containing only 1.8 mg of proteins (amount measured according to Lowry's method).

It should be noted that although the preceding description only gives examples of the use of the process according to the invention for the extraction of enzymes or polypeptide enzyme inhibitor from an aqueous solution, this process may also be used to extract other types of polypeptides, in particular antibodies or antigens, polypeptide hormones such as insulin, proteins such as albumin, glycoproteins and lectins.

I claim:

1. A process for extracting a polypeptide from an aqueous solution, in which a dissolved water-soluble macromolecular complex (I) of macromolecules covalently bonded to molecules of at least one compound capable of fixing the polypeptide in a selective, reversible and non-destructive manner, is selectively reacted with the polypeptide in the solution to fix the polypeptide by forming, in solution, a complex (II); and the complex (II) is separated from the solution, then dissociated into polypeptide molecules and complex (I) molecules, and the polypeptide is isolated.

2. A process according to claim 1 in which the complex (II) is separated as a precipitate by adjusting the pH of the solution.

3. A process according to claim 1 in which an enzyme is extracted using a complex (I) containing molecules of substances selected from the group consisting of reversible inhibitors, substrates and substrate analogues of the enzyme.

4. A process according to claim 1 in which the complex (I) comprises the said molecules, bonded to a macromolecular substance selected from the group consisting of a polyacrylamide, carboxymethyl cellulose, a polyethylene glycol, a polyamine, polyvinyl alcohol and dextran.

5. A process according to claim 1 in which the said molecules are molecules selected from the group comprising p-aminobenzoic acid, o-aminobenzoic acid, trypsin, N-ω-aminohexyl-L-aspartic acid, trypsin-inhibiting soya peptide, p-aminophenyl-thiogalactoside, poly-L-lysine, nicotinamide adenine dinucleotide (NAD) and D-asparagine.

6. A process according to claim 1 in which the complex (I) is formed by grafting molecules of the said compound capable of fixing the polypeptide, onto a macromolecular substance.

7. A process according to claim 1 in which the complex (I) is formed by polymerizing a monomer, to each molecule of which at least one molecule of the said compound capable of fixing the polypeptide is fixed by covalent bonding.

8. A process according to claim 4 in which the complex (I) comprises molecules of p-aminobenzoic acid bonded to a polyacrylamide.

* * * * *